United States Patent
Saucier

(12) 
(10) Patent No.: US 6,854,731 B2
(45) Date of Patent: Feb. 15, 2005

(54) METHOD AND DEVICE FOR PLAYING AN IMPROVED GAME OF BLACKJACK

(76) Inventor: Robert Saucier, 1621 E. Flamingo Rd., Las Vegas, NV (US) 89119

( * ) Notice: Subject to any disclaimer, the term of this patent is extended or adjusted under 35 U.S.C. 154(b) by 0 days.

(21) Appl. No.: 10/035,323

(22) Filed: Dec. 27, 2001

(65) Prior Publication Data

US 2003/0071418 A1 Apr. 17, 2003

Related U.S. Application Data

(63) Continuation of application No. 09/703,373, filed on Oct. 31, 2000, now abandoned.
(60) Provisional application No. 60/162,992, filed on Nov. 1, 1999.

(51) Int. Cl.⁷ .................................................. A63F 1/00
(52) U.S. Cl. ........................................ 273/274; 273/292
(58) Field of Search ............................... 273/274, 292, 273/309; 463/12, 13

(56) References Cited

U.S. PATENT DOCUMENTS

| | | | | |
|---|---|---|---|---|
| 5,806,846 A | * | 9/1998 | Lofink et al. | 273/292 |
| 5,816,575 A | * | 10/1998 | Keller | 273/292 |
| 5,839,730 A | * | 11/1998 | Pike | 273/292 |
| 5,984,308 A | * | 11/1999 | Herrmann | 273/292 |
| 6,158,741 A | * | 12/2000 | Koelling | 273/292 |
| 6,450,500 B1 | * | 9/2002 | Miller | 273/292 |
| 6,481,718 B2 | * | 11/2002 | Koelling | 273/292 |

* cited by examiner

Primary Examiner—William M. Pierce
(74) Attorney, Agent, or Firm—Sierra Patent Group, Ltd.

(57) ABSTRACT

An improved method and device are set forth for playing Blackjack which provides for the player to make a side wager and win an award based upon that wager if the player's first two cards have a sum of twenty.

2 Claims, 2 Drawing Sheets

METHOD AND DEVICE FOR PLAYING AN IMPROVED GAME OF BLACKJACK

This application is a continuation of Ser. No. 09/703,373, filed Oct. 31, 2001, now abandoned which claims benefit of provisional application 60/162,992, filed Nov. 1, 1999.

FIELD OF THE INVENTION

The present invention relates to methods and electronic devices for playing Blackjack related wagering games.

BACKGROUND

The game of Blackjack is a well known and popular game. It is played in a table game version as well on electronic devices. In a casino, the game is played with each player making a monetary wager. The rules for the play of Blackjack are well known. Also in casinos it is known to provide electronic machines at which a player may make a wager and play the game against a computer generated hand representing the dealer's hand. Again this electronic version of the game is played according to the traditional rules for the play of Blackjack. The game has also been embodied into hand-held electronic and computer games where it is played using fictitious credits for fun.

According to the rules of Blackjack, the player is paid even money if his hand total, according to the rules of play, is higher than that of the dealer and less than or equal to a summed value of "21". If the player has a Blackjack, where the player's first two cards dealt are an Ace with a ten-value card for a hand value of "21", the player is paid 3:2 on their wager. Thus, for traditional Blackjack, the highest return a player can expect on their wager is 3:2.

There is a need to provide a game which can be played in either a table game or electronic format which provides the player with an opportunity to receive a jackpot pay and which can provide for such a pay regardless of whether the player wins their Blackjack hand and which is easy to play. Further there is a need for a game which provides a casino with, in relation to Blackjack, an additional opportunity for profit.

SUMMARY OF THE INVENTION

There is, therefore, set forth according to the present invention an improved method and electronic device for playing Blackjack which provides the player with an additional opportunity to win and to win a jackpot greater and which provides the casino with an additional opportunity for profit.

Toward this end the present invention includes method and device for a player to play an improved Blackjack game wherein (i) the player makes a Blackjack wager, (ii) two cards are dealt and displayed to the player and to a dealer defining an initial hands. Each player plays the hand according to the rules of Blackjack to define one or more final hands and the dealer completes the play of the dealer's hand. As with traditional Blackjack, if the player final hand has a higher count than the dealer's (but less than or equal to "21"), the player wins their wager and is paid 1:1 and 3:2 for a Blackjack. If the player and dealer have the same hand counts, the wager is neither won nor lost, i.e. it is a push. If the player's count is less than the dealer's, the player's wager is lost. The improvement according to the present invention provides for the player to make a side, or bonus, wager before cards are dealt. If the player's first two cards have a count of twenty according to the rules of Blackjack, the player wins their side wager and is issued an award, regardless of whether or not the player wins or loses their Blackjack hand. If the player's first two cards do not total twenty, the player loses the side wager and the same is collected by the dealer or retained by the electronic gaming device.

Accordingly, a side or bonus aspect is provided in connection with Blackjack which is easy to understand and which provides the players with an additional opportunity to win and which provides the casino with an additional opportunity for profit by losing, bonus wagers.

BRIEF DESCRIPTION OF THE DRAWINGS

These and other features of the present invention will become better understood with reference to the description, claims and drawings wherein:

DESCRIPTION

Figure 1:
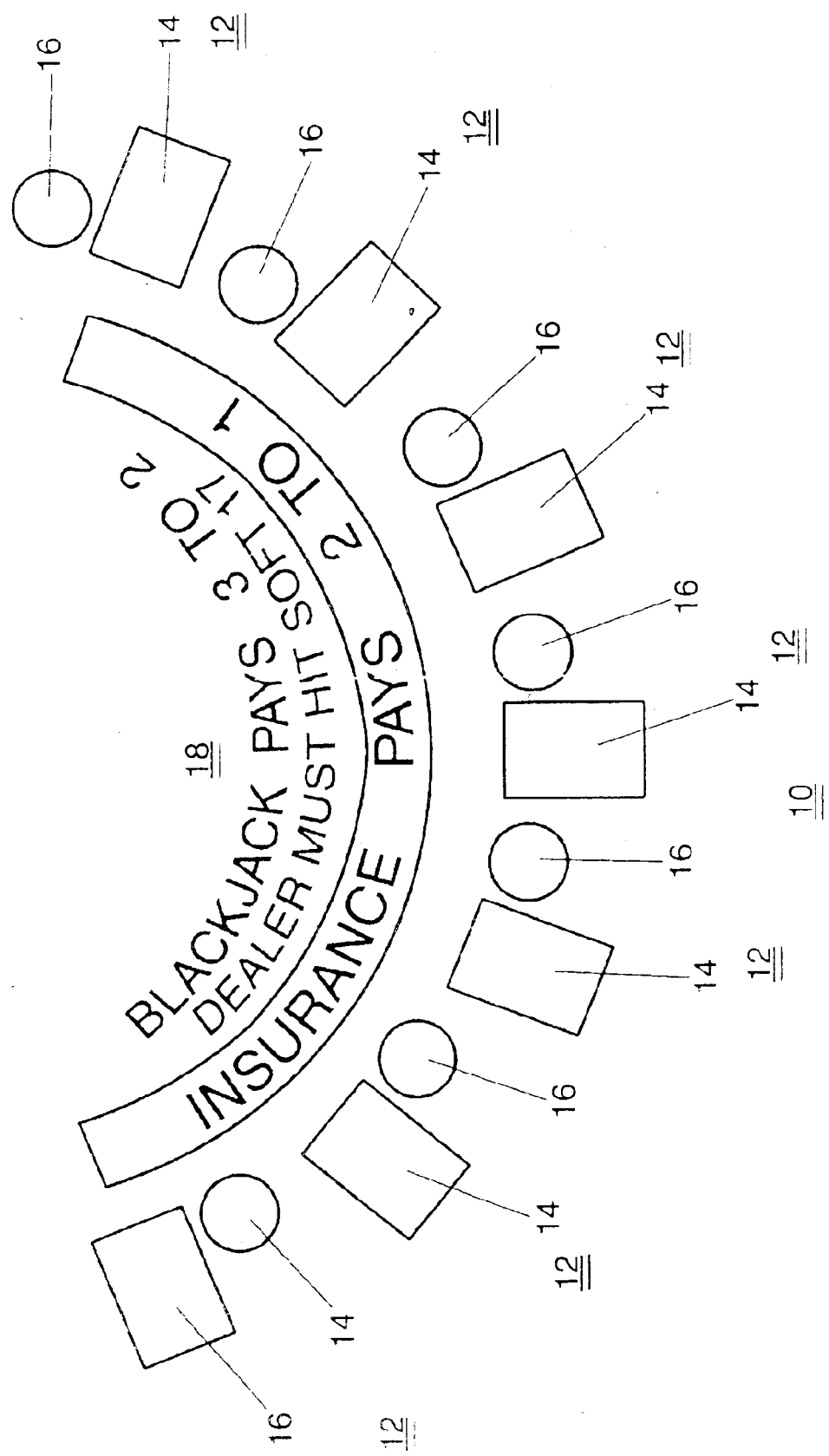
FIG. 1 shows an example of a layout for the play of the casino game.

Turning to FIG. 1 there is shown a layout 10 for the play of the game. This layout 10 may be presented on a table top for live play of the game or may be created at an electronic display for play of an electronic or Internet based version of the game.

The layout 10, for a live table game, has seven player positions 12 to be occupied by players in the fashion of Blackjack. Associated with each player position is a bet receiving area 14 where the player makes there wager to play the basic game of Blackjack according to the well known rules thereof. Also associated with each player position is a side bet area 16 which may be denoted by a depiction of the number "20" as well as a depiction of playing cards such as a pair of Queens of Hearts as shown. Each player may optionally make a side bet in the side wager area 16 in an amount dictated by the casino which may, or may not, have any relation to the amount of the wager the player places in area 14.

The layout 10 further includes a dealer position 18 to be occupied by the dealer of the game and a check tray which hold the chips or checks used in playing the game as is known on the art.

To play the game, the dealer uses a shoe containing a number of decks of playing cards such as, for example, six decks. Any number of decks of two or more may be used. As described below, the pay schedule for awards to winning side wagers, may vary depending upon the number of decks used. The cards contained in the shoe are shuffled as is known in the art. Each player before the dealing of a hand of play by the dealer places a wager in area 14 to participate in the hand. The minimum or maximum amount may be dictated by house rules. Each player also opts to place a wager in the side bet area 16 to participate in the bonus aspects of game. After each player has made their Blackjack wager and, if desired, a side wager as described above, two cards are dealt from the shoe to each player participating in the hand (face up or face down) and to the dealer (face down) in the manner of Blackjack. Each player's hand is played as a Blackjack hand with each player standing, doubling down, splitting, surrendering, taking insurance and/or taking additional cards as is well known in the game of Blackjack. Thus insofar as the Blackjack wager in area 14, the wager is won or lost based upon the rules and known play of Blackjack.

With respect to any side wager, whether the player wins or loses is determined based upon the player's first two cards dealt to him/her and according to the following pay schedules which is based upon the player's side wager:

| First two Cards | Pay Out |
|---|---|
| 2 Decks of Cards | |
| Q♥—Q♥(With a Dealer Blackjack) | 1000:1 |
| Q♥—Q♥ | 200:1 |
| Any Matched 20 | 25:1 |
| Any Suited 20 | 10:1 |
| Any 20 | 4:1 |
| 4 Decks of Cards | |
| Q♥—Q♥(With a Dealer Blackjack) | 1000:1 |
| Q♥—Q♥ | 150:1 |
| Any Matched 20 | 20:1 |
| Any Suited 20 | 9:1 |
| Any 20 | 4:1 |
| 6 Decks of Cards | |
| Q♥—Q♥(With a Dealer Blackjack) | 1000:1 |
| Q♥—Q♥ | 125:1 |
| Any Matched 20 | 19:1 |
| Any Suited 20 | 9:1 |
| Any 20 | 4:1 |
| 8 Decks of Cards | |
| Q♥—Q♥(With a Dealer Blackjack) | 1000:1 |
| Q♥—Q♥ | 125:1 |
| Any Matched 20 | 19:1 |
| Any Suited 20 | 9:1 |
| Any 20 | 4:1 |

All other totals of the first two cards are declared loses of the side wager and the side wager is collected.

As can be appreciated, the side wager is won when the side wager is made and the player's first two cards have a Blackjack value (count) of twenty. By a matched 20 what is meant is that the two cards are the same in suit and ranking, e.g. Jack◊—Jack◊, 10♠—10♠. Suited twenties are where the cards are of the same suit but of a different ranking, e.g. Q♥-J♥. Any twenty is just that and may include unsuited cards having a Blackjack count of ten or an Ace-9 combination.

Figure 2:
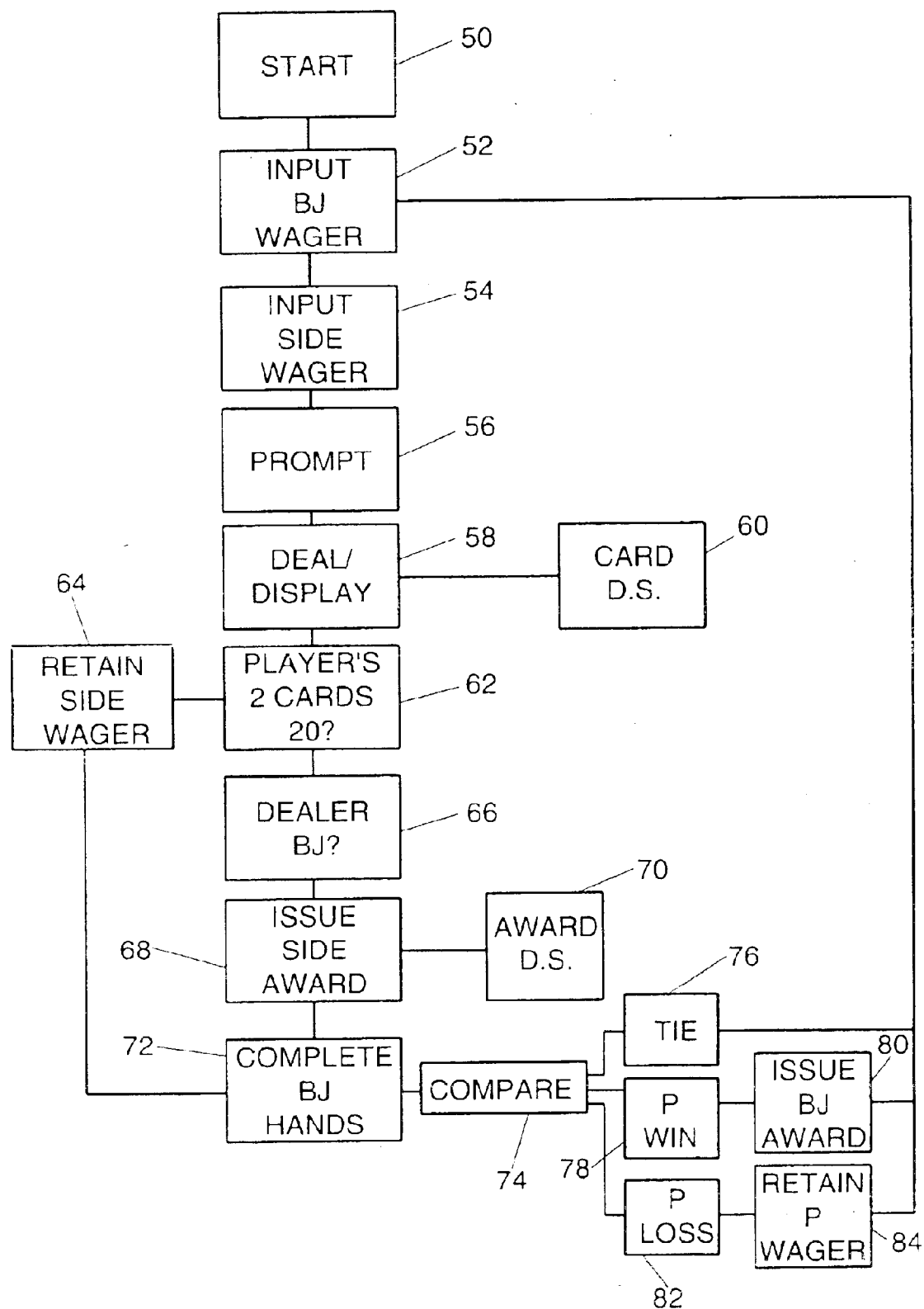
FIG. 2 is a logic diagram for an electronic version of the game.

With reference to FIG. 2, the game can be played in an electronic format or through the Internet as well with the player placing a wager to play Blackjack and an optional side wager. At 50 the machine is started and initialized and at 52 the player inputs his Blackjack wager. The wager may be input by depositing a coin or token into a coin receiver/tester on the machine or by the player wagering credits in a known fashion. If the player desires, at 54 the player inputs their side wager and play of the game is prompted in a manner known in the art. When prompted, the system at 56 selects and displays at 59 the player's initial, two card, holding and a representation of the dealer's initial, two card holding such as by representations of the backs of two playing cards. The cards for display are selected from a first data structure 60 containing data representing the cards of two or more shuffled decks.

Upon the initial display, the processor at 62, if the player has made the side wager, interrogates the player's two cards of his initial holding to determine if those two cards have a sum value (according to the rules of Blackjack) of twenty. If not at 64 the processor controls the system to retain the player's side wager. If the player's initial cards have a sum of twenty the processor at 66 interrogates the dealer's two card initial holding to determine if the dealer has a Blackjack. At 68 the player is issued an award based upon their side wager according to the schedules set forth above. The award is based upon data stored in a second data structure 70 storing data representing the award schedule.

After determination of whether the player has won their side wager and the award, or if the player did not make a side wager, at 72 the player using conventional data input means completes the play of their Blackjack hand according to the rules of Blackjack. The dealer's hand is then completed by the processor as well and at 74 the dealer and player completed, final, hands are compared at 74, also according to the rules of Blackjack. If the player and dealer hands tie as shown at 76, there is no action on the player's Blackjack wager, i.e. it is neither won nor lost. If the player's hand is the winner at 78 the player is issued their Blackjack award at 80 and if the player's hand is the loser at 82 the player's Blackjack wager is retained at 84. The game is then over and the player is prompted to make new wagers.

The side wager is won or lost in either the table version or the electronic version regardless of whether or not the player wins the Blackjack hand. For example, a player may have a matched twenty and win 19:1 on their side wager and the dealer have a 21. The player would lose their base wager but would win on the side wager.

Accordingly the game provides for additional wagering activities which are won or lost regardless of whether the player wins the Blackjack hand. Further the player has an opportunity to win a pay off of 1000:1 by obtaining a specific matched pair when the Dealer also has a Blackjack.

It should be understood that while I have described the game as setting forth the Queen of Hearts pair as the specific matched pair for winning a jackpot that other rankings could be selected such as Jacks, Kings, 10s or the like and other suits could be used.

I claim:

1. A method of placing a wager on a side bet during a blackjack game comprising:
   placing a wager on a side bet;
   dealing two cards to player responsive to said placing said wager;
   dealing two cards to a dealer responsive to said placing said wager;
   determining a value of said two cards dealt to said player;
   determining a value of said two cards dealt to said dealer;
   awarding a payment to said player responsive to a determination of said value of said two cards dealt to said player equaling twenty and a determination of said value of said two cards dealt to said dealer equaling twenty-one; and
   issuing said payment according to the following schedule and based on the amount of said wager:
   same suited queens with dealer twenty-one pays out at least one thousand to one odds;
   same suited queens pays out at least one hundred twenty-five to one odds;
   same value cards pays out at least nineteen to one;
   same suited cards pays out at least nine to one; and
   any value of twenty pay out at least four to one.

2. A product for providing a wager on a side bet during a blackjack game comprising:
   instructions for directing a processor to:
   placing a wager on a side bet;
   dealing two cards to player responsive to said placing said wager;

dealing two cards to a dealer responsive to said placing said wager;

determining a value of said two cards dealt to said player;

determining a value of said two cards dealt to said dealer;

awarding a payment to said player responsive to a determination of said value of said two cards dealt to said player equaling twenty and a determination of said value of said two cards dealt to said dealer equaling twenty-one; and issuing said payment according to the following schedule and based on the amount of said wager:

same suited queens with dealer twenty-one pays out at least one thousand to one odds;

same suited queens pays out at least one hundred twenty-five to one odds;

same value cards pays out at least nineteen to one;

same suited cards pays out at least nine to one; and any value of twenty pay out at least four to one; and a media readable by said processor that stores said instructions.

* * * * *